United States Patent [19]

Tenkman et al.

[11] 4,109,223
[45] Aug. 22, 1978

[54] MULTIPLE CHOKE ASSEMBLY

[75] Inventors: Robert Henry Tenkman, Cincinnati; Alan George Furler, Dayton; Edward F. McGinnis, Jr., Waynesville, all of Ohio

[73] Assignee: NDM Corporation, Dayton, Ohio

[21] Appl. No.: 773,855

[22] Filed: Mar. 3, 1977

Related U.S. Application Data

[63] Continuation of Ser. No. 617,431, Sep. 29, 1975, abandoned.

[51] Int. Cl.² .................. H01F 15/04; H01F 27/28
[52] U.S. Cl. .................. 336/84 C; 128/2.06 B; 128/303.13; 336/96; 336/107; 336/171
[58] Field of Search .................. 336/171, 69, 181, 70, 336/184, 107, 96, 84 C, 221, 222, 180, 170; 128/45, 46, 2.06 B, 303.13, 303.14, 303.17; 179/172, 173, 78 R, 78 A, 80

[56] References Cited

U.S. PATENT DOCUMENTS

| Re. 25,712 | 1/1965 | Slade | 336/170 X |
|---|---|---|---|
| 1,775,880 | 9/1930 | Whitlock | 336/171 |
| 2,403,468 | 7/1946 | Swart | 336/184 X |
| 2,561,537 | 7/1951 | Sands | 336/184 X |
| 3,052,860 | 9/1962 | Walters | 336/222 X |
| 3,089,496 | 5/1963 | DeGelman | 128/303.14 |
| 3,156,886 | 11/1964 | Sutherland | 336/180 X |
| 3,495,264 | 2/1970 | Spears | 336/184 X |
| 3,517,361 | 6/1970 | Reifel et al. | 336/84 |
| 3,576,505 | 4/1971 | Seidel | 336/170 |
| 3,624,577 | 11/1971 | Barrow, Jr. et al. | 336/180 X |
| 3,683,923 | 8/1972 | Anderson | 128/303.14 |

FOREIGN PATENT DOCUMENTS 381,785   10/1932   United Kingdom ............ 336/171

Primary Examiner—Thomas J. Kozma
Attorney, Agent, or Firm—Dybvig & Dybvig

[57] ABSTRACT

A multiple choke assembly comprises individual chokes assembled side by side and in close proximity, mutual inductance phenomena occurring between adjacent chokes being minimized by alternating the lay of adjacent chokes. The disclosure also includes a description of a preferred arrangement utilizing a two-choke assembly for the burn protection of patients undergoing electrosurgery at times when electrocardiograph electrodes may be attached to the patient's skin.

6 Claims, 5 Drawing Figures

MULTIPLE CHOKE ASSEMBLY

This is a continuation of application Ser. No. 617,431 filed Sept. 29, 1975 for MULTIPLE CHOKE ASSEMBLY, now abandoned.

BACKGROUND OF THE INVENTION

1. Field of the Invention

The present invention relates to multiple choke assemblies and to the reduction of mutual inductance effects occurring between chokes assembled in close proximity.

2. Description of the Prior Art

The desirability of placing chokes in series with electrocardiograph electrodes applied to the skin of a patient undergoing electrosurgery has been described in a paper prepared by Becker, Malhotra and Hedley-Whyte and appearing in the journal, "Anesthesiology", Volume 38, No. 2, February 1973. A similar recommendation appears in an article prepared by Finlay, Couchie, Boyce and Spencer and appearing in the journal, "Anesthesiology", Volume 41, No. 3, September 1974. In attempting to implement the recommendations of the foregoing articles, difficulties have been encountered due to the bulkiness of the chokes desired to be attached to the lead wires which are engaged to the patient contact electrodes. Attempts have been made to minimize the effects of such bulkiness by constructing patient blocks which house the requisite number of chokes and which may be conveniently mounted or supported near the patient's body. However, difficulties have been encountered with such patient blocks, such difficulties arising at times when, due to the monitoring configuration desired, one or more chokes of a multiple choke patient block is not to be connected to an electrode or when any one of the electrical connections to electrocardiograph monitoring electrodes is defective. Some of the difficulties appear to be attributable to mutual induction and/or capacitive coupling phenomena occurring between adjacent chokes. It is known, of course, to minimize such phenomena by appropriate shielding. However, the use of shielding in a patient block increases the bulkiness of the block in an undesirable fashion.

It is an object of the present invention to provide a new and improved multiple choke assembly. A further object of the present invention is to provide an improved patient block assembly for protecting patients undergoing electrosurgery from skin burns resulting from a leakage of electrosurgery currents through medical electrodes applied to the patient's body.

SUMMARY OF THE PRESENT INVENTION

In the present invention it has been discovered that the problems arising when one or more chokes of a multiple choke patient block is not in use because not needed or because of a defective connection can be cured or at least substantially eliminated by providing adjacently located chokes with reversed lays. More particularly, the problem is minimized in the present invention by causing adjacently located chokes to be oppositely wound or, in the alternative, by causing adjacently located chokes to be reversely wired.

DESCRIPTION OF THE PREFERRED EMBODIMENTS

Figure 1:
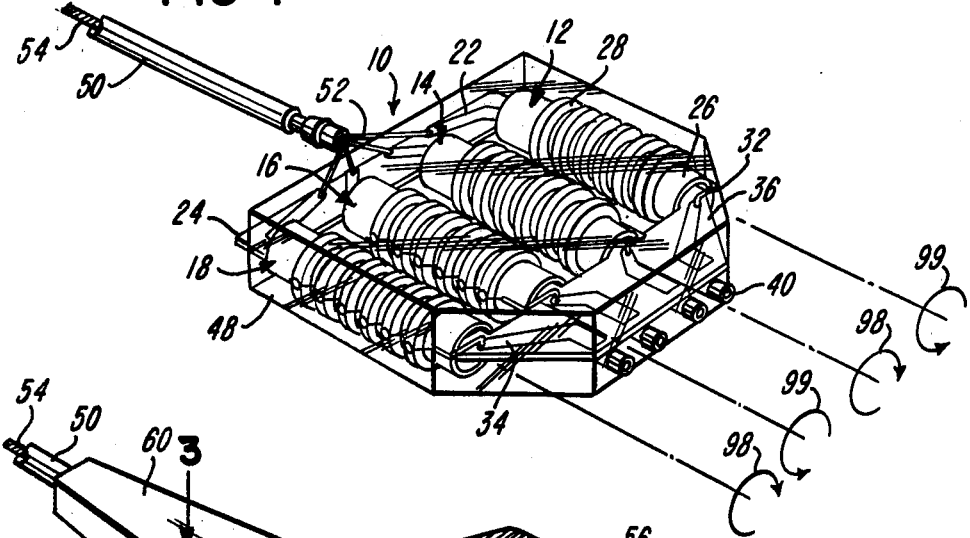
FIG. 1 is a section view with a portion broken away of a potted choke assembly in accordance with the present invention.
Figure 2:
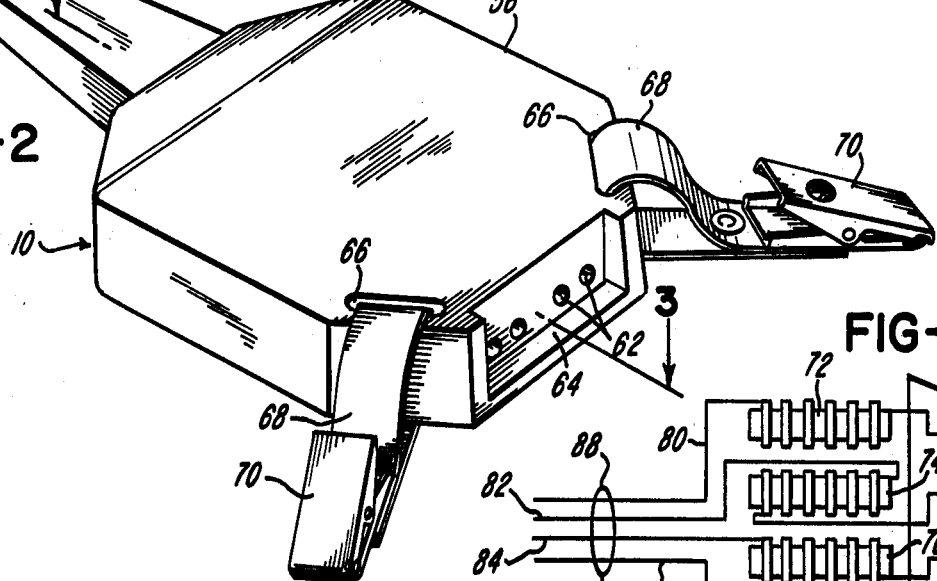
FIG. 2 is a section view with a portion broken away of the same choke assembly after encasement in a protective coating and attachment thereto of drapery clips.
Figure 3:
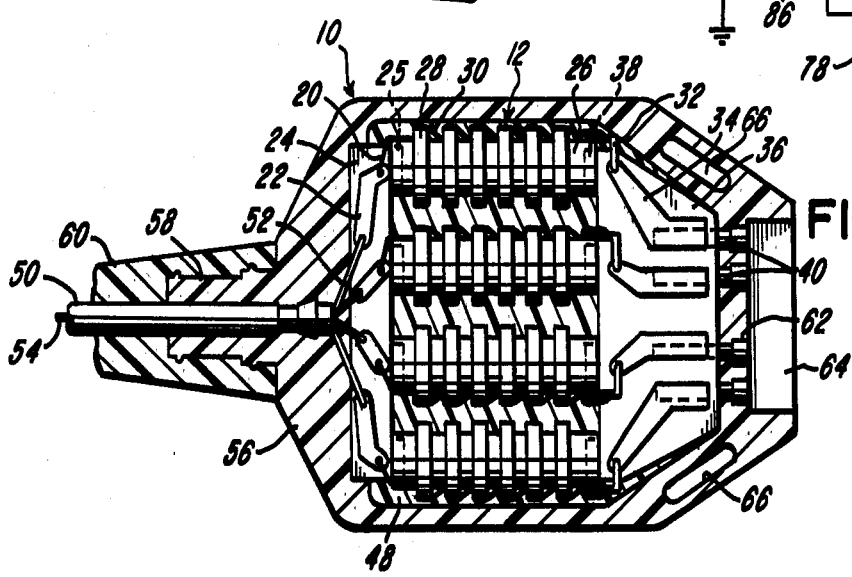
FIG. 3 is a section view taken substantially along the line 3—3 of FIG. 2.

FIGS. 1, 2 and 3 illustrate an assembly 10 of four chokes or inductors 12, 14, 16 and 18 in accordance with the present invention, the figures illustrating various stages through which the assembly progresses. The chokes 12, 14, 16 and 18 each have a generally cylindrical shape and are assembled in spaced apart, axially parallel relation. Except as will be more particularly pointed out in the following remarks, the chokes 12 through 18 may be generally similar in construction; and, accordingly, only the choke 12 will be described in detail.

The choke 12 best appears in FIG. 3. The choke is wound with a single wire 20, which, as is conventional, has an insulating coating such as a polyurethane coating, not particularly illustrated. The wire 20 can be considered as starting from a conductive island 22 to which the wire 20 is soldered by a solder not particularly illustrated. The conductive island 22 is located on a printed circuit board 24.

As appears in FIG. 3, the circuit board 24, which is a nonconductor except for the conductive islands printed thereon, has outwardly projecting tongues 25, there being one tongue for each choke of the four-choke assembly.

Referring particularly to the choke 12, the tongue 25 for such choke enters a nonconducting tube 26, such as a phenolic resin tube, within which is mounted a magnetic core, not shown, which is preferably a ferrite core of the manganese-zinc type.

The wire 20 is wound in conventional fashion layer upon layer to form a first pi section 28. Such winding is preferably in the form of a universal winding, which is well known in the art and therefore not particularly illustrated.

After the outermost layer of the pi section 28 is complete, the wire is indexed to the right as appears in FIG. 3 to form a connector 30, which will connect the first wound pi section 28 to the second wound pi section. A second pi section is then universally wound on the tube 26 and the winding process being described repeated until six interconnected pi sections have been formed on the tube 26. After completion of the last pi section, the wire 20 is soldered or otherwise conductively secured to a conductive post 32, which is mounted upon a conductive island 34 by soldering or the like not particularly shown. The island 34 is located on a printed circuit board 36 having four tongues 38, one of which is seated in the tube 26 of the choke 12.

An eyelet 40, soldered or otherwise conductively secured to the island 34, serves as a termination element for the choke 12.

As previously indicated, the chokes 14, 16 and 18 may be similarly formed; and when all chokes have been wound with starting connections made to spaced apart islands, such as the island 22 located on the printed circuit board 24, and termination connections made to eyelets, such as the eyelet 40 soldered to the island 34 of the circuit board 36, the assembly is potted in conventional fashion to form the potted choke structure illustrated in FIG. 1.

As can be seen, the potting compound 48, which may be an epoxy resin formulation, completely covers the printed circuit board 36 but not the ends of the eyelets 40 projecting outwardly therefrom. At the opposite end of the choke assembly, the potting compound only partly covers the printed circuit board 24, with the result that the four islands from which the four chokes were started have conductive portions projecting outside the potted choke assembly.

After the described potting of the choke assembly, a shielded cable 50 having at least four mutually insulated conductors and preferably a fifth conductor, not shown, which is internally connected to the cable shield, has four of its conductors affixed as by soldering, not shown, to the four islands of the printed circuit board 24. Thus there appears in FIG. 3 an insulated conductor 52 extending from the island 22 to enter the cable 50. Similar connections are made to each of the islands of the printed circuit board 24.

Following the completion of the connections for the shielded cable 50, the potted choke assembly is next placed as a mold core in an injection molding mechanism and a durable covering, such as a polypropylene covering, injection molded about the choke assembly so as to fully surround the same and coat the same with a covering 56. It can be noted that the injection molding mechanism, not shown, forms a hub 58 surrounding the shielded cable 50, the hub 58 being designed to receive and interfit a boot 60, which decorates or streamlines the completed choke assembly. It can also be noted that the covering 56 is shaped to surround and encase the termination eyelets, such as the eyelet 40, for the chokes 12 through 18. It can further be noted that the injection molding mechanism was designed to form sockets, such as shown at 62, which are axially aligned with the termination eyelets and which permit the insertion of conventional connector plugs, not shown, into the termination eyelets for making electrical connection to the choke assembly. To minimize damage to such connector plugs, a wall 64 partially surrounds the array of sockets 62 so that the connector plugs will not be easily bent.

It can also be noted that oblong openings 66 have been formed in the covering 56 on opposite sides of the choke assembly adjacent opposite ends of the wall 64. As apparent in FIG. 2, these openings 66 may conveniently receive straps 68 to which drapery clips 70 are affixed. Such straps and clips are particularly desirable for mounting the choke assembly onto the surgical drape near the patient, and in such event the wall 64 offers the further advantage that the wall can protect the body of the patient from direct contact with any of the connector plugs, not shown, which may be inserted into any of the sockets 62. The choke assembly as it appears in FIG. 2 is sometimes called a patient block.

A four-choke assembly such as has herein been described in reference to FIGS. 1, 2 and 3 was extensively tested for use in protecting patients undergoing electrosurgery from skin burns that have been frequently observed under electrocardiograph electrodes that have been attached to the patient's skin and connected to monitoring equipment under circumstances which could afford a ground path for electrosurgical voltages applied to the patient during electrosurgery. Such testing was conducted throughout the frequency range 150 kilohertz to 2.5 megahertz so as to encompass the majority of electrosurgical generators known to be used and all operating modes, such as cut and coagulation, currently being used in electrosurgical procedures. The reason for four chokes was to accommodate the popular combination of four electrodes used in electrocardiograph work, namely, one electrode on each arm and one electrode on each leg.

In such experimental work, individual chokes, each having ten millihenrys of inductance, were wound in the fashion described in reference to FIGS. 1, 2 and 3 using #36 copper wire with a heavy polyurethane coat. The chokes were wound upon phenolic tubes approximately ⅜ inch (0.952 cm.) in outer diameter, the pi sections being wound to an axial thickness approximately 0.10 inch (0.254 cm.) and an outside diameter approximately 0.5 inch (1.27 cm.), the six pi sections being spaced apart each from the next adjacent approximately 0.08 inch (0.203 cm.) along the length of the phenolic tube. Such individually wound chokes were assembled in groups of four as illustrated in FIG. 1, the separation between chokes being approximately ⅛ inch (0.317 cm.) measured between confronting pi sections of adjacent chokes. Such choke assemblies were found to provide good patient protection only when each choke was placed in series with an electrocardiograph electrode attached to the patient's skin and the shielded bundle of conductors 54 was connected to the input of an electrocardiograph monitor in the conventional fashion used for four-electrode monitoring. In such testing, three basic conditions presenting a hazard to the patient were noted. In some electrocardiographic procedures, only three body contact electrodes are required, e.g. two arm and one reference or leg electrode; and in such cases one of the chokes in the four-choke assembly would be idle and not connected to a body contact electrode. In such instances and depending upon the electrosurgery equipment being used and its mode of operation, steady arcs can be noted to occur between the eyelet of the choke not connected to an electrocardiograph electrode and the eyelet of an adjacent choke. Such arcing can destroy the choke assembly, and also presents an obvious hazard in a hospital room environment.

A similar arcing condition is observed at times when any of the electrocardiograph electrodes has a defective lead wire which presents an open circuit or whenever any of the electrode lead connections is inadvertently withdrawn from the choke assembly.

A further problem results from an EKG electrode which may have been detached from a patient and which may then draw an arc from any nearby ground or the patient himself.

In investigating a four-choke assembly such as described wherein each choke was wound in the same fashion as the other chokes and wherein each choke presents a 10 millihenry inductance, it was noted that if all four chokes were connected at one end to an effective ground, as if connected to an EKG monitor, and if three chokes were connected at their other end to a source of voltage, as if connected to the skin of a patient undergoing electrosurgery through a body contact electrode, while the fourth choke had an open terminal at its other end, as if not connected to the skin of a patient undergoing electrosurgery, the voltage induced in the choke having an open terminal was out of phase with the voltage applied to the other chokes at low frequencies but was in phase with the applied voltage at higher frequencies. In such experiments it was also discovered that if adjacent chokes were oppositely wound, e.g. one choke wound clockwise and the adjacent choke wound counterclockwise, the voltage induced in the open terminal is always in phase with the voltage applied to the immediately adjacent chokes, thus indicating that the directions in which the chokes are wound can have importance if the applied voltage has a relatively low frequency, but loses significance when the applied voltage has a relatively high frequency. A significant observation at the aforementioned intermediate frequency was that when adjacent chokes were oppositely wound the maximum induced voltage at said intermediate frequency was reduced from ten times to two times the voltage applied to adjacent chokes. Investigations such as the foregoing support the following remarks.

The possibility of arcing between two adjacent choke terminals is greatly reduced if the voltage induced in the adjacent terminal has the same phase rather than the opposite phase. The instantaneous difference voltage between terminals rather than the absolute voltage across the chokes determines whether or not the two terminals will arc to each other.

Capacitive coupling between a connected and disconnected terminal will tend to couple the same change in voltage to the disconnected terminal as is on the connected terminal.

Mutual inductance or transformer action between a connected and a disconnected choke terminal (opposite terminals connected to an effective R.F. ground) may or may not tend to couple the same change in voltage to the disconnected terminal as is on the connected terminal depending on the polarity of the inductive coupling which depends on the direction of choke winding and/or whether or not choke terminals are reversed.

Capacitive reactance decreases with increasing frequency. Inductive reactance increases with increasing frequency. The polarity of induced voltage at low frequency depends on the polarity of the inductive coupling. The polarity of induced voltage at high frequency to a high impedance load (e.g. open circuited terminal) is always in phase due to capacitive coupling. The magnitude of the induced voltage when the inductive coupling and the capacitive coupling have the same magnitude due to frequency depends on the polarity of the inductive coupling and the Q of the circuit.

Adjacent chokes have a greater "influence" on each other than distant chokes because of relative magnitudes of inductive and capacitive coupling.

It has been found that the described hazards to the patient can be substantially overcome if attention is paid to the polarity of the inductive coupling. This requires attention to the winding or, more generally, the lays of the chokes assembled side by side in the four-choke assembly. The word "lays" as here used has reference to the polarities of the magnetic fields which will be developed in the chokes. In particular, one should be concerned that the voltage induced at the vacant terminal of any choke which is not electrically connected to a body contact electrode will always be in phase with the driving voltage received from the patient's body by any adjacent choke. Two techniques for assuring the desired lays of adjacent chokes have been identified. One technique is to reverse wind adjacent chokes. Thus, if the choke 12 was wound in the counterclockwise direction, the choke 14 should be wound in the clockwise direction. An equivalent result is achieved if chokes which are not reverse wound are reverse wired.

The phrase "adjacent chokes" refers to chokes which are not separated by an intervening choke. Thus the chokes 12 and 14 are adjacent chokes, but not the chokes 12 and 16, because the choke 14 intervenes and tends to mask the choke 12 from the choke 16. If the choke 14 would be entirely removed from the assembly 10 (and not merely disconnected), the chokes 12 and 16 would then be adjacent chokes which, in accordance with this invention, should be provided with reversed lays.

Figure 4:
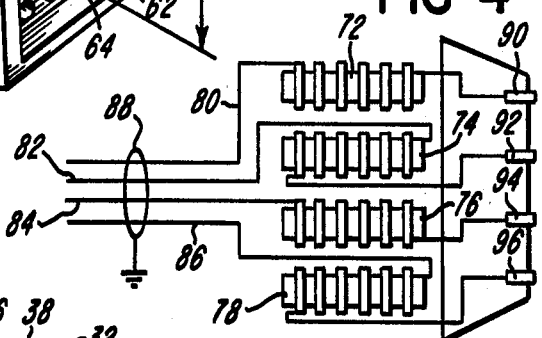
FIG. 4 is a diagrammatic view illustrating reverse wiring in accordance with the present invention.

FIG. 4 illustrates reverse wiring of four chokes 72, 74, 76 and 78, which are not reverse wound. The reference numbers 80, 82, 84 and 86 schematically illustrate the four wires from a shielded cable such as the cable 50 illustrated in FIG. 3 and thus represent the wires used for connection to electrocardiograph monitoring apparatus. The reference numbers 90, 92, 94 and 96 schematically illustrate termination eyelets such as the eyelet 40 illustrated in FIG. 3, which are provided for completing electrical connections to skin contact electrodes. As an example of reverse wiring, the monitor lead 80 is connected to the leftmost pi section of the choke 72 as it appears in FIG. 4, and the eyelet connection to the same choke is made to the rightmost pi section of that choke. The connections to the adjacent choke 74 are reversed. Thus a monitor connection is made to the rightmost pi section, and the eyelet connection is made to the leftmost pi section. Since the requirement of reverse lays dictates that the wiring to the choke 76 be reversed as compared to the wiring to the choke 74, the monitor lead 84 goes to the leftmost pi section, while the eyelet lead goes to the rightmost pi section. Similarly, the wiring to the choke 78 is again reversed, connecting the monitor to the rightmost pi section and the eyelet to the leftmost pi section.

By a logical extension, the lay of any given choke is the reverse of the lay of an adjacent choke either if there is reverse wiring or reverse winding; and within any given multiple choke assembly, it is unimportant which way the reversal of lay as between adjacent chokes is achieved.

Returning to the potted choke assembly illustrated in FIG. 1, this assembly was initially described without reference to lay. To complete the description of the preferred embodiment, it is now necessary to impose upon the description as originally given, the further requirement that the chokes 12 through 18 be assembled with adjacently opposite lays.

As a means of diagrammatically indicating that the chokes 12, 14, 16 and 18 of the preferred embodiment have reversed lays as between adjacent chokes, arcuate arrows 98 and 99 have been illustrated in FIG. 1, the arrows 98 indicating a lay in one direction and the arrows 99 indicating a lay in the opposite direction.

Figure 5:
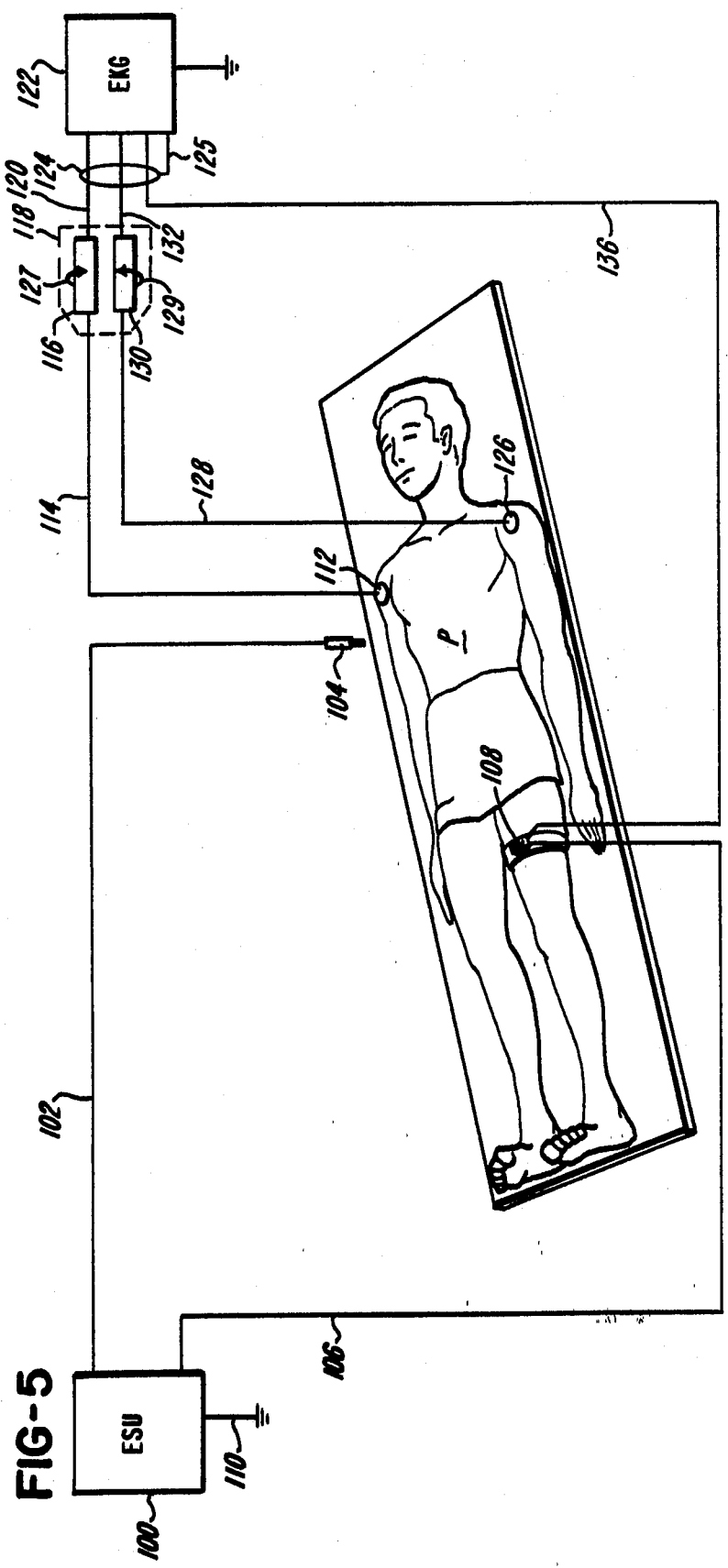
FIG. 5 is a diagrammatic and pictorial view illustrating a preferred utilization of a two-choke patient block.

FIG. 5 illustrates a preferred manner in which a two-choke assembly in accordance with the present invention can be utilized during electrosurgery to protect a patient from skin burns resulting from electrocardiograph electrodes attached to the patient's body. The reference number 100 identifies a box labeled ESU, which schematically indicates an electrosurgical generator. The generator 100 generates a high frequency current which is applied over conductors 102 and 106.

The current is applied to the body of a patient P by means of an electrode 104 commonly referred to as an active electrode. The electrosurgical currents received in the patient's body from the electrode 104 are intended to return to the electrosurgical unit through a patient dispersive electrode or grounding pad 108 contacted to the skin of the patient and to the conductor 106. By way of connections not shown, the conductor 106 is connected to the earth ground 110 internally of the electrosurgical generator 100.

The dispersive pad 108 may be of the type disclosed in U.S. Pat. No. 3,895,635 issued July 22, 1975, which is hereby incorporated herein by reference.

FIG. 5 illustrates electrocardiograph electrodes 112 and 126 of the skin contact type, which are placed on the patient's right and left arms. The electrode 112 is connected by a conductive lead 114, a choke 116 and a conductor 120 to an electrocardiograph monitoring unit schematically shown by a box 122 marked EKG. The conductor 120 is one of three mutually insulated conductors residing in a shielded cable diagrammatically shown at 124, the cable shield being connected to an electrical reference of the monitoring unit through a conductor 125.

The second electrocardiograph electrode 126 is placed on the patient's left arm and is connected by a conductive lead 128, a second choke 130 and a conductor 132 passing through the shielded cable 124 to the electrocardiograph monitor. The two chokes 130 and 116 are shown as assembled side by side in a patient block 118 constructed generally in the manner of the four-choke assembly 10 of FIG. 1 but comprising only two chokes. Arcuate arrows 127 and 129 in FIG. 5 illustrate that the chokes 116 and 130 have reversed lays.

In accordance with this preferred arrangement, a third connection to the EKG normally used for the connection of a third skin contact electrode against which the electrodes 112 and 126 are referenced is used to make a conductive connection through a conductor 136 included in the shielded cable 124 to the dispersive electrode 108. If the electrocardiograph monitor 122 is of the type that ties the reference electrode conductor 136 to ground, the electrocardiograph unit itself provides a redundant path to ground. Thus, should the ground connection through 106 and 110 fail, a backup protection is afforded through the ground for the electrocardiograph monitor 122. In this arrangement the dispersive electrode 108 is serving a double function. First, it provides the necessary ground path for the electrosurgical generator; and, secondly, the dispersive electrode 108 functions as the reference electrode to which the signals passing through the chokes 116 and 130 are referred.

FIG. 5 involves a somewhat conventional circumstance in which both the electrosurgical generator 100 and the electrocardiograph monitor 122 are tied to an earth ground. There are, of course, numerous types of electrosurgical generators, only some of which are tied to an earth ground, and numerous types of electrocardiograph monitors, only some of which are tied to an earth ground. Those electrosurgical generators and electrocardiograph monitors which are not directly tied to an earth ground utilize an internal instrument ground which is isolated from earth ground.

Regardless whether earth grounds or internal instrument grounds are involved, a two-choke patient block connected to electrodes as described in reference to FIG. 5 and connected to an electrocardiograph unit through a cable whose shield is connected to the ground system for the electrocardiograph unit is found to satisfactorily protect patients undergoing surgery from skin burns under skin contact electrodes, provided of course that the patient grounding pad is connected to the electrocardiograph unit as a reference electrode.

Although the preferred embodiments of this invention have been described, it will be understood that various changes may be made within the scope of the appended claims.

Having thus described our invention, we claim:

1. A patient block for minimizing the passage of electrosurgery currents through electrocardiograph electrodes contacting the body of a patient undergoing electrosurgery, comprising: a plurality of electrically separate and spaced apart chokes, and potting means surrounding said chokes and filling the spaces between said chokes, each said choke having a start portion and a termination portion, each said choke having first means projecting through said potting means for electrical connection of one of its start and termination portions to one of said electrodes, and each said choke having second means projecting through said potting means for electrical connection of the other of its start and termination portions to an electrocardiograph monitor, adjacent chokes in said patient block having opposite lays so as to minimize arcing between said adjacent chokes should one of said chokes not be electrically connected to a body contact electrode.

2. The patient block of claim 1 wherein the first means are disposed at one end of said patient block and the second means are disposed at the opposite end of said patient block.

3. The patient block of claim 2 wherein the second means includes shielded cable means for conducting electrical signals between said chokes and said electrocardiograph monitor.

4. The patient block of claim 2 wherein said chokes are elongate bodies disposed in generally parallel relation with the longitudinal axes of said chokes disposed generally coplanar.

5. The patient block of claim 2 wherein said potting means includes a cover having spaced apart sockets disposed at said one end, said first means comprising eyelets disposed interiorly of said sockets, there being one eyelet for each choke and one socket for each eyelet.

6. The patient block of claim 5 wherein said sockets are disposed in a spaced apart array and said cover includes wall means partially surrounding said array for protecting connector plugs when inserted into said sockets.

* * * * *